(12) United States Patent
Lambert

(10) Patent No.: US 9,192,701 B2
(45) Date of Patent: Nov. 24, 2015

(54) NASAL ASPIRATOR FOR BABIES

(76) Inventor: Cyril Lambert, Bordeaux (FR)

(*) Notice: Subject to any disclaimer, the term of this patent is extended or adjusted under 35 U.S.C. 154(b) by 191 days.

(21) Appl. No.: 13/983,061

(22) PCT Filed: Jan. 31, 2012

(86) PCT No.: PCT/FR2012/050203
§ 371 (c)(1),
(2), (4) Date: Aug. 1, 2013

(87) PCT Pub. No.: WO2012/104540
PCT Pub. Date: Aug. 9, 2012

(65) Prior Publication Data
US 2013/0310747 A1    Nov. 21, 2013

(30) Foreign Application Priority Data

Feb. 2, 2011 (FR) ...................................... 11 50796

(51) Int. Cl.
*A61M 1/00* (2006.01)
(52) U.S. Cl.
CPC ..... *A61M 1/0076* (2013.01); *A61M 2210/0618* (2013.01)
(58) Field of Classification Search
CPC ............ A61M 1/0001; A61M 1/0066; A61M 1/0023; A61M 1/0003; A61M 2210/0618; A61M 1/0068; A61M 1/0072; A61M 1/0076; A61M 1/0039; A61M 1/0064; A61M 1/0011; A61M 1/0017

USPC .............................................. 604/35–39, 317
See application file for complete search history.

(56) References Cited

U.S. PATENT DOCUMENTS

| 3,833,001 | A | 9/1974 | Abrahams | |
|---|---|---|---|---|
| 5,183,467 | A | 2/1993 | Mouney | |
| 2007/0173760 | A1* | 7/2007 | Fedenia et al. | 604/131 |
| 2007/0287959 | A1* | 12/2007 | Walter et al. | 604/131 |
| 2008/0312674 | A1* | 12/2008 | Chen et al. | 606/162 |
| 2009/0202665 | A1* | 8/2009 | Javer et al. | 424/744 |

FOREIGN PATENT DOCUMENTS

FR   2549727   2/1985

OTHER PUBLICATIONS

International Search Report dated Apr. 27, 2012, corresponding to PCT/FR2012/050203.

* cited by examiner

*Primary Examiner* — Nicholas Lucchesi
*Assistant Examiner* — Morgan Lee
(74) *Attorney, Agent, or Firm* — Young & Thompson

(57) ABSTRACT

A device for suctioning nasal secretions, including a nasal tip having an opening through which the nasal secretions are suctioned, a first pipe, a first end of which is connected to the nasal tip and the other end of which communicates via a first opening, and a second pipe, one end of which communicates via a second opening, and these two pipes form an angle no more than 90°, and the opening connected to the nasal tip is aligned with the second pipe and arranged with the air stream exiting the opening of the second pipe.

19 Claims, 4 Drawing Sheets

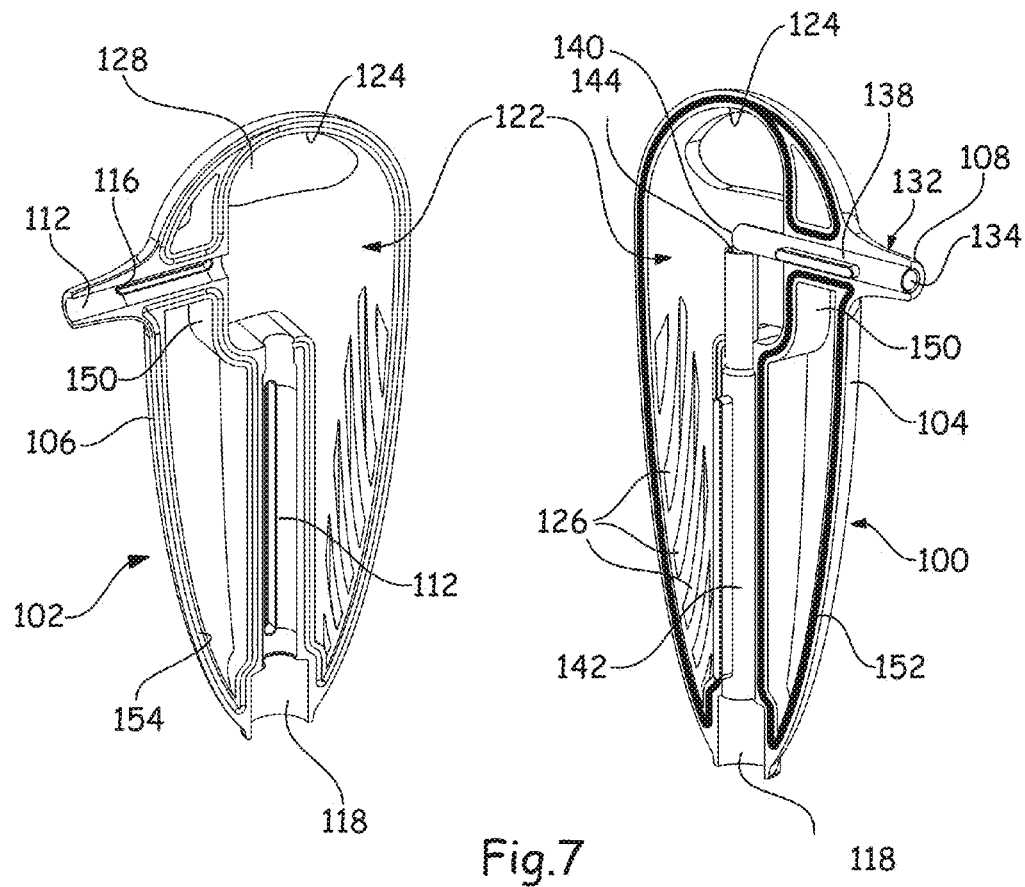
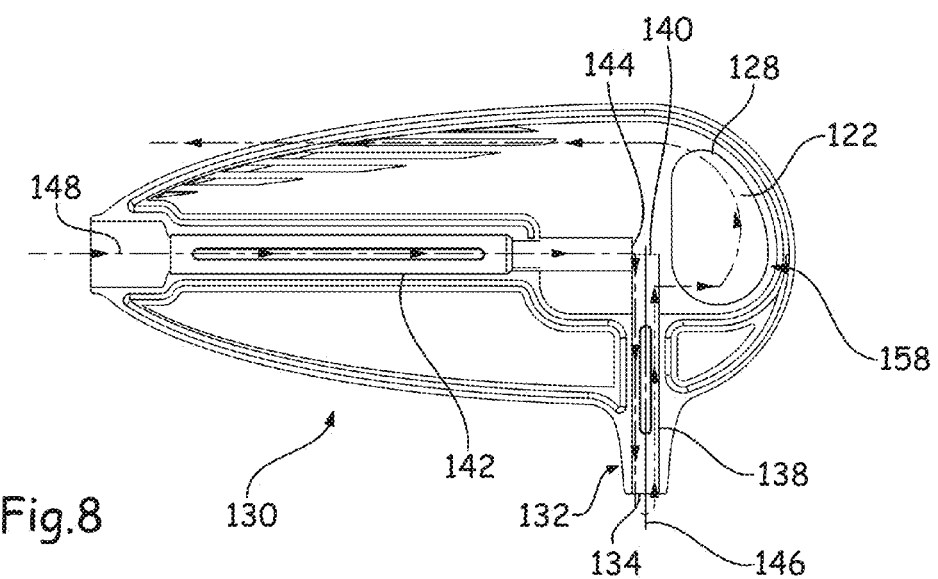

NASAL ASPIRATOR FOR BABIES

BACKGROUND OF THE INVENTION

This invention relates to a device that makes it possible to suction nasal secretions, commonly called a nasal aspirator for infants.

DESCRIPTION OF THE RELATED ART

Figure 1:
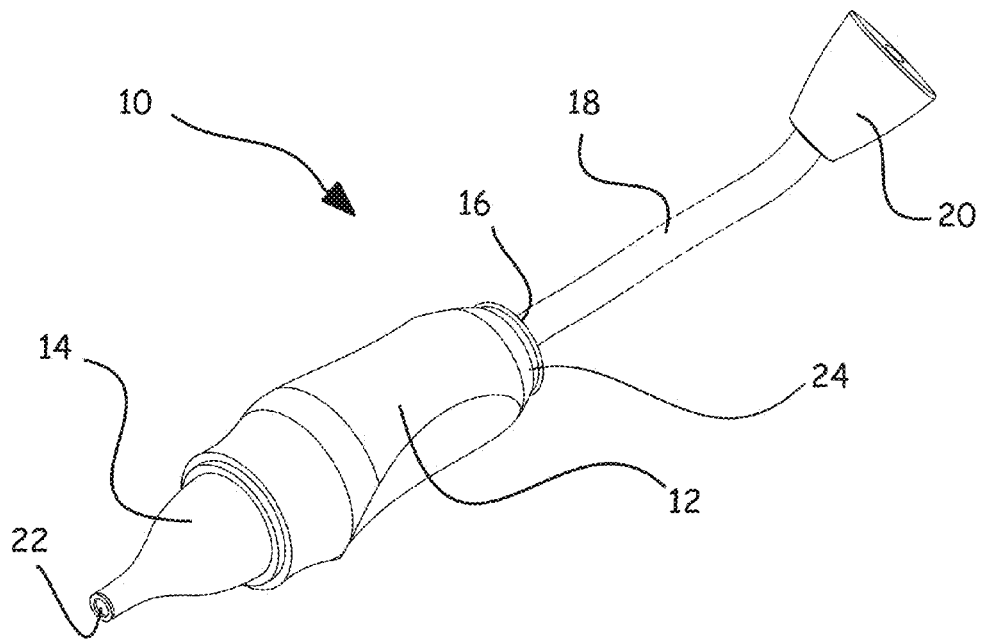

As illustrated in FIG. 1, a nasal aspirator 10 for infants of the prior art comprises a hollow body 12 with, at a first end, a nasal tip 14 and, at the other end, an opening 16, with a flexible tube 18 connecting the opening 16 to a mouth tip 20.

At one end, the nasal tip 14 comprises an outside diameter that is reduced in such a way as to be inserted into an infant's nostrils. This same end also comprises an opening 22 via which nasal secretions are suctioned. According to an embodiment, the hollow body 12 comes in the form of a hollow cylinder, with the nasal tip 14 being joined to a first end, a plug 24 in the shape of a hemisphere with the opening 16 being joined to the other end.

The operation of a nasal aspirator for infants is relatively simple. The end of the nasal tip 14 is inserted into one of the infant's nostrils, and the mouth tip 20 is put into the mouth by the individual responsible for extracting the nasal secretions.

The latter by suctioning brings about the extraction of secretions from the nostril that pass via the nasal tip into the hollow body 12.

To limit the transfer of secretions to the mouth of the individual who is doing the suctioning, the body comprises a filter in the form of a foam plug whose outside diameter is adapted to the inside diameter of the hollow cylinder forming the hollow body 12.

This simple solution is not satisfactory because this filter does not make it possible to retain the small-sized elements such as the viruses that migrate from the infant's nostril to the mouth of the individual who is doing the suctioning and that contaminate said individual.

To remedy this drawback, certain nasal aspirators for infants comprise motorized suctioning means. Even if this solution makes it possible to limit the risks of contamination of the individual who uses the nasal aspirator for infants to the extent that there is no longer a need to do suctioning, it is not entirely satisfactory because it leads to increasing the price of the nasal aspirator for infants in a significant manner.

According to the prior art, different devices for suctioning secretions that are described in, for example, the documents U.S. Pat. No. 5,183,467, U.S. Pat. No. 3,833,001, and FR-2, 549,727 are known. According to these documents, the flow of a fluid that, owing to a Venturi effect, entrains an air flow that generates suctioning is used for bringing about the suctioning. According to these documents, the fluid that is used is water, and the water flow comes from a faucet or from a pump. Other documents propose using air as an entrainment fluid. However, as above, the air flow is brought about by a pump. Taking into account means used for bringing about the Venturi effect, these devices require a pump or any other mechanism for producing the air flow that can generate a suctioning flow owing to a Venturi effect.

SUMMARY OF THE INVENTION

The purpose of this invention is to remedy the drawbacks of the prior art by proposing a nasal aspirator for infants that is of a simple design so as to limit its costs while reducing the risks of contamination of the individual who uses it.

For this purpose, the invention has as its object a device that makes it possible to suction the nasal secretions, comprising a nasal tip with an opening via which nasal secretions are suctioned, a first pipe of which a first end is connected to the nasal tip, with the other end emptying via a first opening, and a second pipe with an end emptying via a second opening, characterized in that the two pipes form an angle that is less than or equal to 90°, and the opening that is connected to the nasal tip is placed in the extension of the second pipe and in the air stream exiting from the opening of the second pipe in such a way as to bring about a Venturi effect and a suctioning phenomenon in the first pipe that is connected to the nasal tip.

BRIEF DESCRIPTION OF THE DRAWING FIGURES

Figure 2:
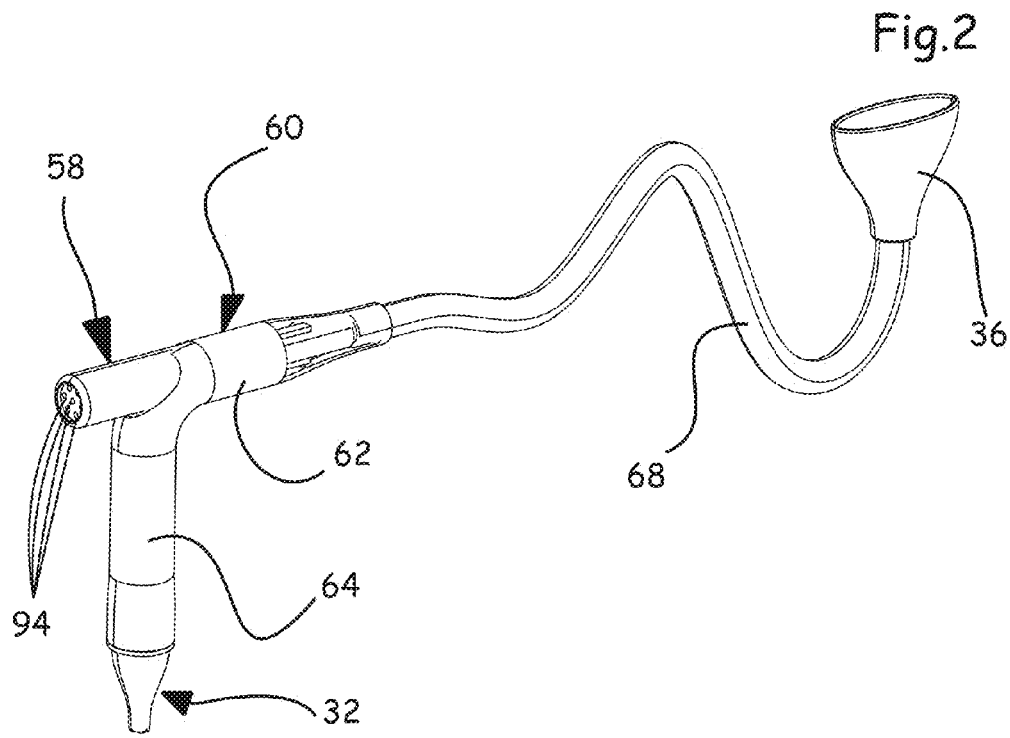
Figure 3:
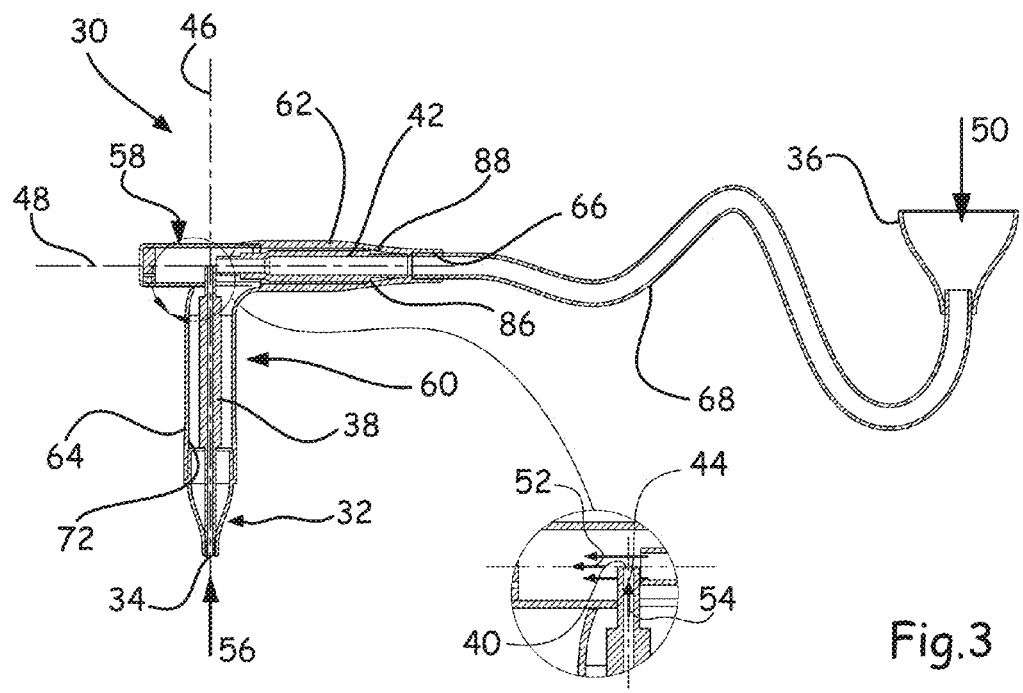
Figure 4:
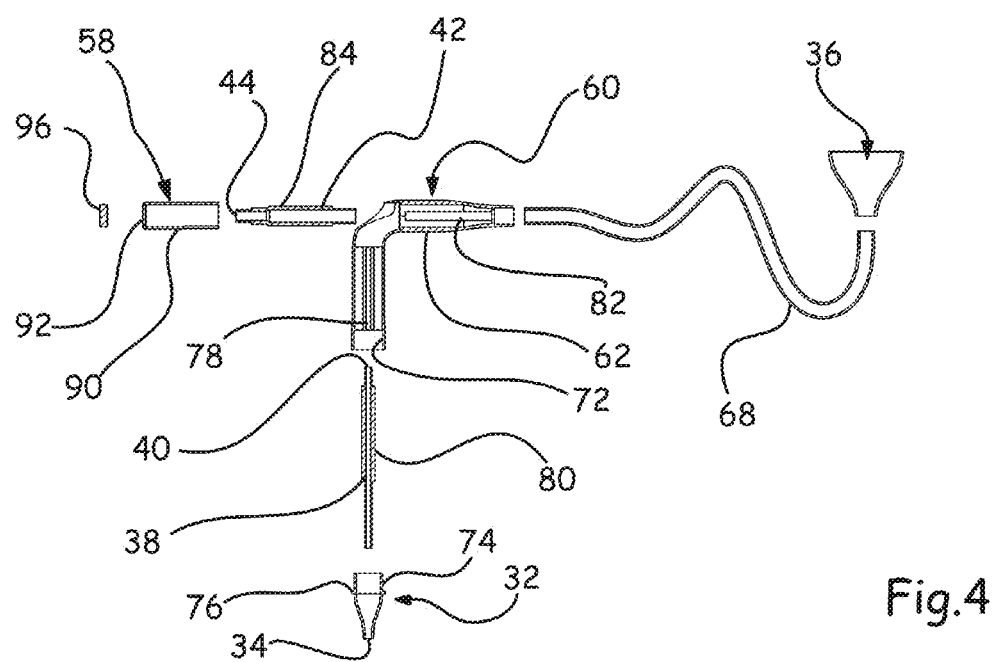
Figure 5:
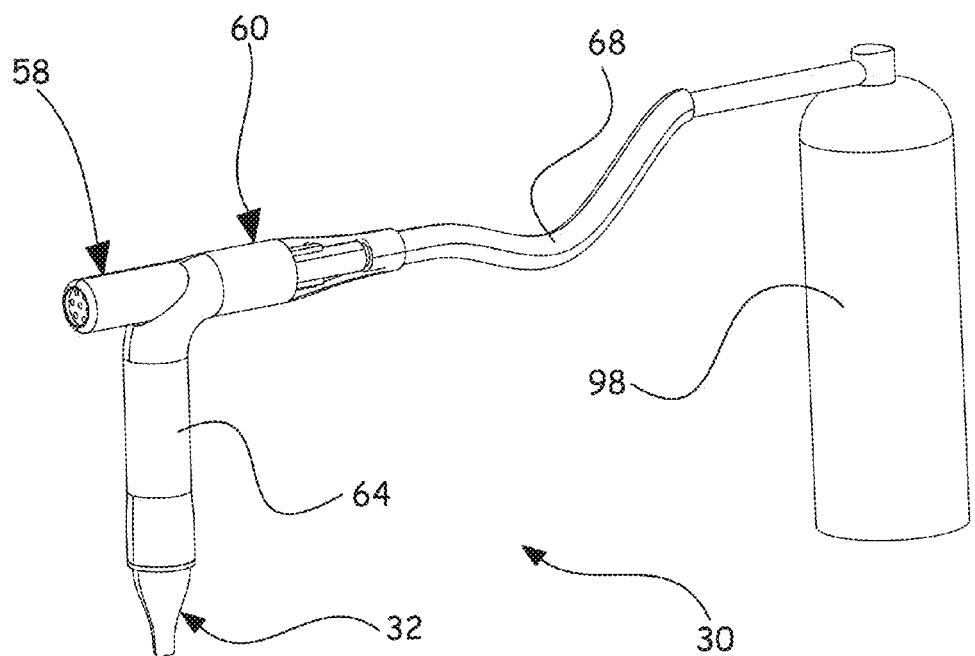
Figure 6:
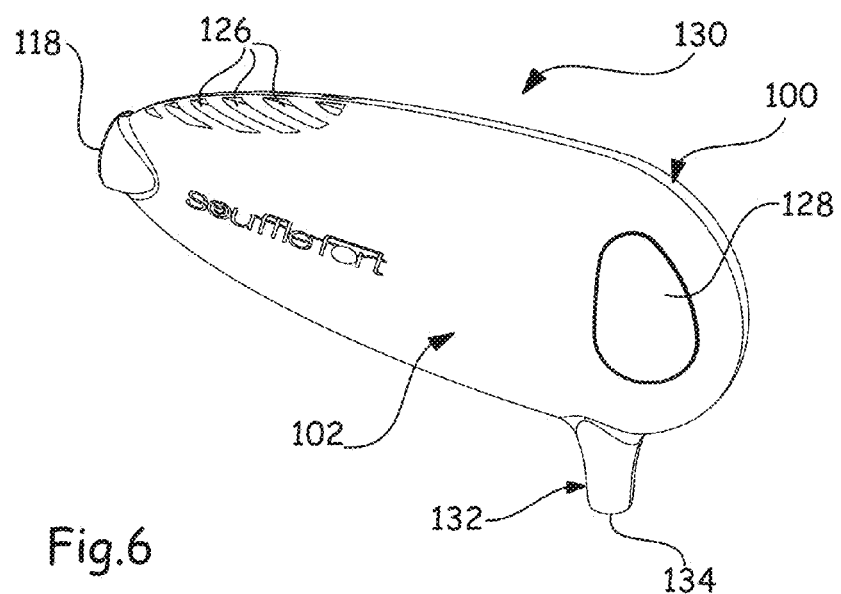

Other characteristics and advantages will emerge from the following description of the invention, a description that is provided only by way of example, relative to the accompanying drawings in which:

FIG. 1 is a perspective view of a nasal aspirator for infants according to the prior art, FIG. 2 is a perspective view of a nasal aspirator for infants according to the invention, FIG. 3 is a cutaway view of the nasal aspirator for infants of FIG. 2, FIG. 4 is a cutaway view of the different elements of the nasal aspirator for infants of FIG. 2, FIG. 5 is a perspective view of a variant of the invention, FIG. 6 is a perspective view of a nasal aspirator for infants according to another variant of the invention, FIG. 7 is a perspective view that illustrates the nasal aspirator for infants of FIG. 6 in the open position, and FIG. 8 is a cutaway of the nasal aspirator for infants of FIG. 6.

DETAILED DESCRIPTION OF THE INVENTION

In a known manner, a nasal aspirator 30 for infants comprises, on the one hand, a nasal tip 32 with, at one end that can be inserted into an infant's nostril, an opening 34 via which nasal secretions are suctioned, and, on the other hand, a mouth tip 36 that can be placed at least partially in the mouth of an individual using the nasal aspirator 30 for infants.

According to the invention, the nasal aspirator 30 for infants comprises, on the one hand, a first pipe 38 of which a first end is connected to the nasal tip 32, with the other end emptying via an opening 40, and, on the other hand, a second pipe 42 of which a first end is connected to the mouth tip 36, with the other end emptying via an opening 44. The two pipes 38 and 42 and the two openings 40 and 44 are placed in such a way that an air flow exiting from the opening 44 that is connected to the mouth tip 36 brings about a Venturi effect and a suctioning phenomenon in the first pipe 38 that is connected to the nasal tip 32.

For this purpose, the two pipes 38, 42 form an angle that is less than or equal to 90°, and the opening 40 that is connected to the nasal tip is placed in the extension of the second pipe 42, in the air stream exiting from the opening 44 that is connected to the mouth tip 36. Preferably, the two pipes 38, 42 are placed approximately at 90°.

This arrangement of the pipes makes it possible to be able to generate satisfactory suctioning by blowing into the mouth tip 36.

According to an embodiment, the two pipes 38 and 42 each come in the form of a hollow cylinder respectively with axes 46 and 48. The opening 40 is delimited by a peripheral edge placed in a plane that is perpendicular to the axis 46. The opening 44 is delimited by a peripheral edge that is placed in a plane that is perpendicular to the axis 48. Preferably, the peripheral edge that delimits the opening 40 that is connected to the nasal tip 32 is placed in a plane that contains the axis of the pipe 42 that is connected to the mouth tip 36. This arrangement makes it possible to improve the Venturi effect.

Advantageously, the cross-section of the pipe 38 at the opening 40 is smaller than that of the pipe 42 at the opening 44. Preferably, the diameter of the pipe 38 at the opening 40 is equal to approximately half the diameter of the pipe 42 at the opening 44. This arrangement makes it possible to improve the Venturi effect.

In contrast to the prior art, the user no longer does the suctioning at the mouth tip for bringing about the suctioning of nasal secretions at the nasal tip. He just has to blow into the mouth tip to bring about the suctioning of nasal secretions at the nasal tip, which limits the risks of contamination during use.

As illustrated in FIG. 3, when the user blows into the mouth tip (as illustrated by the arrow 50), an air flow exits from the pipe 42 via the opening 44 (as illustrated by the arrows 52). This air flow exiting from the pipe 42 brings about a Venturi effect at the pipe 38 that generates a flow exiting from said pipe 38 (indicated by the arrow 54) and a suctioning at the nasal tip (indicated by the arrow 56).

Advantageously, the nasal aspirator 30 for infants comprises a reservoir 58 that makes it possible to collect the suctioned nasal secretions into which reservoir the pipes 38 and 42 are directed via the openings 40 and 44.

Preferably, the pipes 38 and 42 are rigid at least at the openings 40 and 44.

According to an embodiment that is preferred and illustrated in FIGS. 2 to 4, the nasal aspirator 30 for infants comprises an L-shaped rigid body 60, with a first hollow branch 62 in which the pipe 42 is housed and a second hollow branch 64 in which the pipe 38 is housed.

The branch 62 comes in the form of a tube with circular cross-sections, and, at the end that is not connected to the branch 64, it comprises an opening 66 that makes possible the passage of the second pipe 42 and/or a flexible tube 68 connecting said pipe 42 to the mouth tip 36. The other end of the pipe 62 opens in such a way as to accommodate the reservoir 58 by nesting.

The branch 64 comes in the form of a tube with circular cross-sections, and, at the end that is not connected to the branch 62, it comprises an opening 72 that makes it possible to join a nasal tip 32.

According to one embodiment, the nasal tip 32 comprises a tapered shape with the opening 34 at one end and a seat 74 limited by a collar 76 at the other end, whereby said seat can be joined in the branch 64 to the collar 76. The nasal tip 32 is not described in more detail because it may be identical to that of the prior art.

The pipes 38 and 44 are positioned in the rigid body 60 in such a way that the openings 40 and 42 are positioned correctly.

According to an embodiment, the branch 64 and/or the pipe 38 comprise(s) means for positioning the pipe 38 in a plane that is perpendicular to the axis 46. In addition, the branch 64 and/or the nasal tip 32 comprise(s) means for positioning the pipe 38 in the direction of the axis 46 in such a way that the opening 40 of the pipe 38 is correctly positioned relative to the opening 44 of the pipe 42.

For this purpose, the branch 64—at its inside wall—comprises ribs 78 that make it possible to center the pipe 38. In parallel, the pipe 38 comprises—at its outside wall—ribs 80 that make it possible to center it in the branch 64. In addition, one end of the pipe 38 is joined in the opening 34 of the nasal tip for positioning it in the direction of the axis 46.

In parallel, the branch 62 and/or the pipe 42 comprise(s) means for positioning the pipe 42 in a plane that is perpendicular to the axis 48 and in the direction of the axis 48 in such a way that the opening 44 of the pipe 42 is correctly positioned relative to the opening 40 of the pipe 38.

For this purpose, the branch 62 comprises—at its inside wall—ribs 82 that make it possible to center the pipe 42. In parallel, the pipe 42 comprises—at its outside wall—ribs 84 for being centered in the branch 62.

For positioning the pipe 42 along the axis 48, the latter comprises a reduction of its outside diameter that forms a shoulder 86 that rests against a wall 88 that is provided inside the branch 62.

In addition, one end of the pipe 42 is joined in the opening 66 of the branch 62 for positioning the pipe 42 in the direction of the axis 48. The flexible tube 68 is joined in the pipe 42 at the opening 66.

According to an embodiment, the reservoir 58 comes in the form of a cylinder 90 that is closed at one end by a wall 92 with openings 94 making possible the passage of air and whose outside diameter is adjusted to the inside diameter of the pipe that forms the branch 62 in such a way as to be joined in said pipe.

The cylindrical wall 90 of the reservoir comprises a U-shaped cut-out in such a way as to allow the passage of the pipe 38.

A filter 96 in the form of a foam pellet is advantageously provided inside the reservoir 58, flattened against the wall 92.

According to one embodiment, the elements that constitute the nasal aspirator for infants are made of plastic material. The bonds between these different elements are produced by joining or by nesting in such a way as to simplify the assembly and disassembly and to allow easy cleaning.

According to another variant illustrated in FIG. 5, the nasal aspirator 30 for infants cannot comprise a mouth tip 36. For generating the air flow exiting from the second pipe 42 via the opening 44, it is possible to connect the other end of the pipe 42 to a reservoir 98 of pressurized gas. This reservoir 98 can come in the form of an aerosol whose output valve is connected to the pipe 42 directly or by means of a flexible tube that is analogous to the flexible tube 68. This reservoir can contain dry pressurized air.

According to another embodiment that is described in FIGS. 6 to 8, a nasal aspirator 130 for infants comprises, as above, two pipes 138 and 142 with, respectively, axes 146 and 148, the first being connected to a nasal tip 132, the second to a mouth tip 136, and of which the respective openings 140 and 144 are arranged in accordance with the invention. According to this embodiment, the nasal aspirator 130 for infants comprises two half-shells 100 and 102 that are assembled along a junction plane P that contains the axes 146 and 148 and that have walls 104 and 106 that are essentially symmetrical relative to the plane P. The two walls 104 and 106 each have an outside surface that constitutes the outside surface of the nasal aspirator for infants. When the two half-shells are assembled, the nasal aspirator for infants has an elongated egg shape. The size of the nasal aspirator for infants in the direction of the axis 148 is at least two times larger than the size in the direction of the axis 146. This elongated egg shape is essentially flattened in the direction that is perpendicular to the plane P.

This egg shape is essentially symmetrical relative to a plane that is perpendicular to a plane and that passes through the axis 148.

To provide an order of magnitude in a non-limiting manner, the egg shape has a length on the order of 12 cm in the direction of the axis 148, and a width on the order of 5 cm in the direction of the axis 146.

The egg shape comprises an appendage that forms the nasal tip 132. This appendage has a tapered shape with a flat surface 108 that is perpendicular to the plane and parallel to the axis 148, containing the opening 134 of the nasal tip. Advantageously, the nasal tip 132 consists of two symmetrical parts relative to the plane. These two parts are integrated with two half-shells 100 and 102 and are obtained in a single piece with the latter.

Preferably, the nasal tip 132 comprises a hypoallergenic coating at its outside surface.

According to a preferred embodiment, the pipe 138 extends from the flat surface 108 to the axis 148. It has a length on the order of 4 cm, an inside diameter on the order of 4.5 mm, and an inside diameter on the order of 3.5 mm.

The pipe 142 is placed on the inside of the egg shape. It has a length on the order of 7.7 cm, and its end oriented toward the first pipe 138 preferably comes into contact with the latter.

According to a characteristic of the invention, the second pipe 142 has a diameter at its opening 144 that is smaller than the diameter provided at the other end that is connected to the mouth tip.

Thus, the second pipe has an inside diameter on the order of 4.5 mm at the opening 144 and an inside diameter on the order of 5.5 mm at the other end. This reduction in diameter makes it possible to increase the flow rate of the air flow inside the second tube 142, which contributes to improving the suctioning action.

According to a preferred embodiment, the two pipes 138 and 142 are integral with a half-shell 100 and are made in a single piece with this half-shell 100. In addition, the other half-shell 102 comprises furrows 112 whose shapes correspond to the outside surfaces of the pipes 138 and 142.

To ensure the relative positioning of the two half-shells 100 and 102, the outside surfaces of the two pipes 138 and 142 comprise projecting shapes, for example on the first and second pipes, that work with hollow shapes 116 at the furrows 112.

In the extension of the second pipe 142, the two half-shells each comprise a semi-cylindrical hollow 118 that makes it possible to join a flexible tube that connects the second pipe 142 to the mouth tip 136.

The inside of the two half-shells 100 and 102 forms a reservoir 122 that makes it possible to collect secretions.

The reservoir 122 has shapes that make it possible to orient the air flow that exits from the second pipe 142 in such a way that it makes a half-turn as illustrated in FIG. 8. This arrangement makes it possible to separate secretions from the air flow.

For this purpose, the reservoir has a curved profile 124 facing the pipe 142 in such a way as to impress a half-turn on the air flow.

To ensure the discharge of the air flow outside of the nasal aspirator 130 for infants, at least one air exhaust 126 is provided on at least one half-shell. Advantageously, the two half-shells 100 and 102 comprise air exhausts 126 that are distributed in an essentially symmetrical manner relative to the plane P.

To reinforce the effect obtained by the curved profile 124, the air exhausts 126 are placed opposite the curved profile 124 in an area of the reservoir that is offset relative to the end 144 of the pipe 142 in the direction of the other end of the pipe 142.

To display the secretions, at least one half-shell 100 or 102 comprises a transparent portion 128 at the wall 104. Preferably, each half-shell 100 and 102 comprises a transparent portion 128.

Preferably, the inside of the two half-shells 100 and 102 comprises at least one partition 150 that makes it possible to reduce the volume of the reservoir so as to limit the area to be cleaned. Thus, the reservoir 122 is delimited by the second pipe 142 and a partition 150 that is secant with the first pipe 138 and that extends to the curved profile 124. According to an embodiment, the partition 150 consists of two parts, one for each half-shell 100 and 102, contiguous with the junction plane P.

To ensure sealing, the peripheral edge of the half-shell 100 comprises at least one rib 152 that is housed in at least one groove 154 provided at the peripheral edge of the half-shell 102.

Advantageously, the ribs 152 extend over the periphery of the half-shell 100, on both sides of each pipe 138 and 142 and at the partition 150. It is the same with grooves 154.

Preferably, the ribs 152 have a height that is less than that of the projecting shapes 114 that ensure the positioning of the two half-shells 100 and 102.

The invention claimed is:

1. A device to suction nasal secretions comprising:
a nasal tip (32, 132) with an opening (34, 134) which nasal secretions are suctioned;
a first pipe (38, 138) with a first end being connected to the nasal tip (32, 132), and a second end emptying via a first opening (40, 140);
a second pipe (42, 142) with a first end with a first opening (66) and an opposite, second end emptying via a second opening (44, 144) through which an air stream exits,
wherein the first and second pipes (38, 42, 138, 142) form an angle that is less than or equal to 90° at a junction where the first opening (40, 140) of the first pipe is placed abutting the second opening of the second pipe and in the air stream exiting from the second opening of the second pipe;
a reservoir (58, 122) at the junction of the first and second pipes, the reservoir collecting suctioned nasal secretions emptied from the first opening (40, 140) of the first pipe, the reservoir (122) comprising a curved profile (124) facing the second pipe (142), wherein the reservoir (122) is delimited by two half-shells (100, 102) assembled along a junction plane containing respective axes (146, 148) of the first and second pipes (138, 142), and the two half-shells (100, 102) comprise at least one partition (150) that reduces a volume of the reservoir (122), the at least one partition (150) is secant with the first pipe (138).

2. The device according to claim 1, wherein the first and second pipes (38, 42, 138, 142) form an approximately 90° angle.

3. The device according to claim 1, wherein the first opening (40, 140) of the first pipe (38, 138) is delimited by a peripheral edge placed in a plane that contains the axis (48, 148) of the second pipe (42, 142).

4. The device according to claim 1, wherein the first pipe (38, 138) at the first opening (40, 140) of the first pipe (38, 138) has a cross-section that is smaller than a cross-section of the second pipe (42, 142) at the second opening (44, 144).

5. The device according to claim 4, wherein the second pipe (142) comprises a reduction in diameter.

6. The device according to claim 1, wherein the curved profile (124) causes the air flow through the second pipe (142) to carry out a half-turn so as to separate the secretions from the air flow.

7. The device according to claim 1, wherein the first and second pipes (138, 142) are integral with a first of the two half-shells (100) and are made in a single piece with said first half-shell (100).

8. The device according to claim 7, wherein first and second pipes (138, 142) have outside surfaces that comprise projecting shapes that work with hollow shapes (116) provided at a second of the two half-shells (102).

9. The device according to claim 1, wherein at a peripheral edge, a first of the two half-shells (100) comprises at least one rib (152) that is housed in at least one groove (154) provided at a peripheral edge of a second of the two half-shells (102).

10. The device according to claim 8, wherein at a peripheral edge, a first of the two half-shells (100) comprises at least one rib (152) that is housed in at least one groove (154) provided at a peripheral edge of a second of the two half-shells (102).

11. The device according to claim 10, wherein the first and second pipes (38, 42, 138, 142) form a 90° angle.

12. The device according to claim 11, wherein the first opening (40, 140) of the first pipe (38, 138) is delimited by a peripheral edge placed in a plane that contains the axis (48, 148) of the second pipe (42, 142).

13. The device according to claim 10, wherein the first opening (40, 140) of the first pipe (38, 138) has a cross-section that is smaller than a cross-section at the second opening (44, 144) of the second pipe (42, 142).

14. The device according to claim 13, wherein the second pipe (142) comprises a reduction in diameter.

15. The device according to claim 10, wherein the curved profile (124) causes the air flow through the second pipe (142) to carry out a half-turn so as to separate the secretions from the air flow.

16. A device to suction nasal secretions comprising: a nasal tip (32, 132) with an opening (34, 134) which nasal secretions are suctioned; a first pipe (38, 138) with a first end being connected to the nasal tip (32, 132), and a second end emptying via a first opening (40, 140); and a second pipe (42, 142) with a first end with a first opening (66) and an opposite, second end emptying via a second opening (44, 144) through which an air stream exits, wherein the first and second pipes (38, 42, 138, 142) form an angle that is less than or equal to 90 at a junction where the first opening (40, 140) of the first pipe is placed abutting the second opening of the second pipe and in the air stream exiting from the second opening of the second pipe, wherein the first and second pipes (138, 142) are integral with a first of two half-shells (100) and are made in a single piece with said first half-shell (100).

17. The device according to claim 16, further comprising a reservoir (58, 122), the reservoir collecting suctioned nasal secretions emptied from the first opening (40, 140) of the first pipe, the reservoir (122) comprising a curved profile (124) facing the second pipe (142), wherein the reservoir (122) is delimited by two half-shells (100, 102) assembled along a junction plane containing respective axes (146, 148) of the first and second pipes (138, 142), wherein the curved profile (124) causes the air flow through the second pipe (142) to carry out a half-turn so as to separate the secretions from the air flow.

18. The device according to claim 16, wherein the first and second pipes (38, 42, 138, 142) form an approximately 90° angle.

19. The device according to claim 16, wherein,
the first pipe (38, 138) at the first opening (40, 140) of the first pipe (38, 138) has a cross-section that is smaller than a cross-section of the second pipe (42, 142) at the second opening (44, 144).

* * * * *